United States Patent [19]

Schoepe et al.

[11] Patent Number: 4,504,596
[45] Date of Patent: Mar. 12, 1985

[54] CUPREOUS CATALYST AND PROCESS FOR MAKING SAME

[75] Inventors: George P. Schoepe, Raleigh, N.C.; Don H. Hashiguchi, University Heights, Ohio

[73] Assignee: SCM Corporation, New York, N.Y.

[21] Appl. No.: 574,809

[22] Filed: Jan. 30, 1984

[51] Int. Cl.$^3$ .......................... B01J 21/04; B01J 21/06; B01J 23/02; B01J 23/72
[52] U.S. Cl. .................................... 502/225; 502/226; 502/231; 502/242; 502/244; 502/331; 502/340; 502/343; 502/345; 502/346; 556/476
[58] Field of Search ............... 502/331, 345, 346, 225, 502/226, 231, 242, 244, 340, 343, 346; 556/476; 241/14

[56] References Cited

U.S. PATENT DOCUMENTS 2,443,902  6/1948  Ferguson et al. ............... 502/345 X
2,889,350  6/1959  Horny et al. .................... 502/346 X

*Primary Examiner*—W. J. Shine
*Attorney, Agent, or Firm*—R. A. Sturges; M. H. Douthitt

[57] ABSTRACT

Improved catalyst is made by including in a grind charge of cupreous particulates a small proportion of hydrated refractory metal oxide such as hydrated alumina. Said grind charge contains a major proportion of cuprous and cupric oxides, a minor proportion of elemental copper, and up to about 10% of promoter material. Such charge is subjected to high energy comminution with concomitant crystal lattice distortion. The catalyst is useful for the production of alkyl and aryl halosilanes.

10 Claims, No Drawings

CUPREOUS CATALYST AND PROCESS FOR MAKING SAME

This invention relates to an improvement on that of U.S. Ser. No. 548,604 filed on Nov. 4, 1983, now abandoned by Erhard Klar, Don H. Hashiguchi, and Ronald J. Dietrich. That earlier application related to particulate cupreous catalyst and a method for making same, more particularly to such catalyst for producing an alkyl or aryl halosilane (such as dimethyl dichlorosilane from methyl chloride and silicon) at elevated temperature. The teachings of that application are incorporated herein expressly by reference.

A variety of copper/copper oxide catalysts have been proposed for such silane production. They have been made from precipitated cupreous materials, from elemental copper variously produced, from alloys rich in copper, and from copper oxide-rich materials. The instant invention adds a special promoter effect to such silane catalyst which also has had crystal lattice distortion induced into it by high energy comminution.

One aspect of the instant invention is an improved process for producing a catalyst for cupreous particulates containing a major proportion of cuprous and cupric oxides and a minor proportion of elemental copper wherein a grind charge of particulates having average particle size above 15 microns and containing up to about 10% promoter-providing material is subject to high energy comminution with concomitant crystal lattice distortion until the average particle size of the resulting grind is no larger than 15 microns. Such improvement comprises including in said charge about 0.05–5% of hydrated refractory metal hydroxide.

Another aspect of the instant invention are cupreous catalysts useful for alkyl or aryl chlorosilane production. One such catalyst is a high cuprous oxide catalyst consisting essentially of about 80–90% cuprous oxide, about 2–10% cupric oxide, about 2–10% elemental copper, and up to about 10% promoter including about 0.05–5% of hydrated refractory metal oxide, said catalyst having surface area of about 1–8 square meters per gram, average particle size not substantially above about 15 microns, and exhibiting crystal lattice distortion. Another such catalyst has a medium content of cuprous oxide; it consists essentially of about 30–75% copper oxide, about 10–45% cupric oxide, about 4–25% elemental copper, and up to about 10% promoter including about 0.05–5% of hydrated refractory metal oxide, said catalyst having surface area of about 1–8 square meters per gram, average particle size not substantially above about 15 microns, and exhibiting crystal lattice distortion.

DETAILED DESCRIPTION OF THE INVENTION

For efficiency and economy, the cupreous particulates providing the grind charge (i.e., the charge to the high energy milling operation) generally are no longer than about 80 mesh, advantageously −150 mesh, and preferably preponderantly −325 mesh (so such charge will not unduly restrict production in the high energy milling operation). Average particle size of such grind charge is above 15 microns and ordinarily 90% or more of it will be at least about 25 microns or coarser. Desirably these particulates should not contain more than about a percent of adventitious (that is, normally or inherently present, but not deliberately added) material for best control of charge analysis. The grind charge desirably is extremely low in lead and other impurities that are considered detrimental for silane catalysts. The grind charge can contain, if desired, up to about 10% and usually just a few percent of promoter-providing material such as elemental aluminum or zinc or the oxides or chlorides of these metals, a little (e.g., 0.5%) iron, copper chloride, even a little antimony (below 0.05%), and silica or aluminosilicates typically up to a few percent maximum. The promoter can be an original part of the grind charge of cupreus particulates, or it can be added thereto prior to the high energy comminution that follows. In some instances it can be efficient to add a promoter-providing material such as iron and/or metal as particles of an alloy of such metal with at least part of the particulate copper that is to be further processed by pyrometallurgy to make such grind charge for the high energy milling.

The particular new type of promoter that has been found here to be a surprisingly useful additive to a grind charge of cupreous particulates just prior to its high energy comminution is a small dosage of hydrated refractory metal oxide. Typically, it can be as low as about 0.05%, and it can reach about 5% by weight of such grind charge. Whether such material helps the catalyst by keeping particles thereof free flowing in use, and/or whether it acts to form the sites which are beneficially attached by a reactant such as a chloride in the halosilane manufacture, or whether the enhancement of the catalyst is due to another reason is not known at present.

The preferred hydrated refractory metal oxide is a hydrated alumina, most preferably an alumina trihydrate for efficiency and economy. While the temperature in the high energy comminution in some instances can rise to as high as, say, 150° only minor dehydration of such hydrated oxide is to be expected in such operation, and what of such oxide remains in the final catalyst is expected to be hydrated to some degree even though it is possibly not as fully hydrated as the hydrated oxide charged to the high energy comminution operation.

The other hydrated refractory metal oxides for the instant promotional purposes here are the hydrated oxides of the metals titanium, zirconium, and beryllium. It might be noted that $Al_2O_3$, $TiO_2$, $ZrO_2$, and $BeO$ have negative free energy of formation at 25° of about 101–139 kilocalories per gram atom of oxygen in their structure. Some of these hydrated oxides, e.g. alumina trihydrate or monohydrate, have a defined equivalent water content; others are indicated to be amorphous, and their equivalent water content is not numerically defined. Normally the instant hydrated oxides are obtainable in the form of fine powders; sometimes they are referred to as "hydrous oxides", or "hydroxides", or an "acid" such as a "titanic acid" or a "zirconic acid". In any case they should not be confused with an anhydrous or practically anhydrous oxide such as $Al_2O_3$. Advantageously the dosage of the hydrated refractory metal oxide in the grind charge for high energy comminution is between about 0.2 and 1% of such charge for efficiency and economy; less than about 0.05% can be too little to expect appreciable beneficial effect; more than about 5% does not appear to be needed and can act as a diluent, but it is conceivable to tolerate even more if desired.

Advantageously the cupreous material for making the grind charge is directly from pyrometallurgical processing, i.e., it is pyrometallurgically-sourced for efficiency and control of product quality. By this is meant that the ultimate chemical step in making such cupreous material prior to using it as a grind charge here is, for example, effected by the heating of copper metal and/or a copper compound such as a copper oxide or carbonate in an inert and/or a chemically reactive atmosphere (usually a reducing or an oxidizing one) or in the substantial absence of any atmosphere. One typical source of such cupreous material is the mill scale that forms on the surfaces of hot copper ingots that are exposed to air; another is from the air-oxidized surfaces of hot copper machining chips and cuttings; another is the controlled air oxidation of copper particles; still another is from the collection of vaporized copper and/or a dust of an oxide of copper. The cupreous material for making a grind charge can be from a single source as, for example, the air oxidation of fine copper particles, or it can be a blend of products from a plurality of sources. Even cupreous material that has been generated initially by a hydrometallurgical process (such as by precipitation from an aqueous solution) can be considered as being from a pyrometallurgical source for the instant purposes if such material is further processed with heating, for example to reduce or to oxidize it with a gas for conditioning for the high energy milling.

The grind charge advantageously has been comminuted previously to fairly small size in a mill with a short retention time such as a hammermill using swing or fixed hammers. Other conventional pulverizing apparatus also can be used for such operation preparatory to the high energy milling. Thus, one can use a roller mill, an attrition mill, or a fluid energy mill.

Especially advantageous for the instant process is the careful selection of a grind charge of analysis as outlined herein coupled with the fineness of grind made by the energy comminution of such charge (to give adequate surface area and crystal lattice distortion to the catalyst product). Desirably such comminution is operated continuously, that is, with continuous feed to and take-off from the high energy milling (comminuting) apparatus. Batch milling can be used for this step if desired, however. Illustrative of a useful batch mill is the Sweco (the trademark of Sweco, Inc.) vibratory mill. A continuous high energy comminution apparatus preferred is a so-called "Palla mill", the product of Humboldt-Wedag of West Germany. A smaller laboratory size batch vibratory mill that can be useful is the Megapac (a trademark of Pilamec Ltd.) mill. Such mills generally are called "vibratory ball mills"—although the grinding media inside the shell(s) if often other than spherical in shape. Such media typically is made of a hard ceramic (such as alumina, zirconia), a steel (such as a stainless steel, a low alloy steel, a nickel steel), tungsten carbide, etc., all conventional grinding media. Such mill generally oscillates with a compound motion that is imparted to the shell(s) by an eccentric mechanism.

Another high energy mill useful for the instant purpose is the "Szegvari mill" made by the Union Process Company. It is basically a stirred ball mill, and it even can be modified in accordance with the precepts of U.S. Pat. No. 3,927,837. In summary, the high energy comminution in the instant process is done by an apparatus that has solid grinding media in it, is driven with substantially more horsepower per unit weight of grinding medium than is a conventional tumbling ball mill, and provides a prolonged residence time (actually an average residence time in a continuous operation) for the grind charge typically of at least about 10 minutes to an hour or even longer if necessary or desired.

In a matter of a half hour to an hour a large high energy mill can comminute the grind charge to size much smaller than 10 microns average size, usually 2–7 microns. If additional size reduction is needed, the output can be recycled for remilling.

In a preferred processing operation for making the catalyst the grind charge has particle size no coarser than 150 mesh, and the particulates thereof contain about 75–95% cuprous oxide, about 4–10% cupric oxide, and about 4–10% elemental copper.

In another useful processing operation for making the catalyst the grind charge has at least about 95% of its particles not substantially larger than 325 mesh and the particulates charged contain about 30–75% cuprous oxide, about 10–45% cupric oxide, and about 4–25% elemental copper. To obtain the particular stoichiometry of such charge it is often necessary to blend two or more powders of differing oxide and elemental copper contents.

The following example shows the process embodiment and the catalyst embodiment now preferred for efficiency and economy, but should not be construed as limiting the invention. In this specification all parts are parts by weight, all percentages are weight percentages, all temperatures are in degrees Celsius, and all mesh sizes are U.S. Standard Sieve sizes unless otherwise expressly noted; additionally, in this specification an average particle size means the mass median particle size as measured with the Microtrac (a trademark of Leeds & Northrup Company) particle size analyzer, and Specific Surface Area (SSA) is measured by the BET (Brunauer, Emmett, and Teller) method.

EXAMPLE

The grind charge was fine (at least 98% of the particles were −325 mesh), and it had the approximate copper analysis of 10% elemental copper ($Cu^o$), 49.5%, $Cu_2O$, and 40% CuO. The minute remainder was normal trace impurities (picked up in processing or occurring normally in the raw material used) including nitric acid insolubles, iron, tin, and a little lead. The charge had been made by hammermilling tiny airoxidized copper particles.

The grind charge was fed continuously several times through a Model 35U Palla mill (steel shot as the grinding media) and withdrawn continuously therefrom. The net product output was about 68 kilos per hour. This output from said Palla mill was useful as a catalyst for the reaction of methyl chloride with silicon to produce dimethyldichlorosilane. Such catalyst exhibited crystal lattice distortion, and it had the following analysis:

| Ingredient | Wt. % | |
|---|---|---|
| $Cu^o$ | 9.3 | |
| $Cu_2O$ | 63.5 | |
| CuO | 27.4 | (total to here 100.2%) |
| Nitric Acid Insolubles | 0.04 | |
| Fe | 0.03 | |
| Sn | 0.035 | |
| Pb | 0.01 | |
| SSA, $m^2$/gm. | 3.2 | (Specific surface area) |
| Particulate size, microns | 3.9 | (mass median diameter) |

An aliquot was taken from the Palla mill output and dosed with 0.3% alumina trihydrate, a monoclinic crystalline material made by the Bayer process (which involves an alkali treatment of bauxite under pressure). The trihydrate had density of about 2.4 grams per cc and the following typical analysis:

| | |
|---|---|
| Fe (as Fe$_2$O$_3$) | 0.02% |
| SiO$_2$ | 0.01–0.02% |
| Na$_2$O | 0.2–0.3% |
| Free Moisture | 0.03% |
| Loss on Ignition | 34% |
| Al$_2$O$_3$ | 65% |
| Particle Size | (99% −100 mesh) |
| | (62% −325 mesh) |

The thus-dosed aliquot was then subjected to a light regrinding in a laboratory batch vibratory ball mill (a Megapac mill) for about 30 minutes (wherein the temperature did not rise substantially above about 65° at any time). The dosed and reground product has slightly greater specific surface area (3.6 m$^2$/gm. vs. 3.2), very slightly smaller particle size, and clearly more nitric acid insolubles (0.22% vs. 0.04 although such insolubles analysis is not highly accurate). It also exhibited crystal lattice distortion. Such product was far more effective and efficient as a catalyst for the reaction of methyl chloride with silicon to produce dimethyldichlorosilane than was the undosed catalyst from which it was made; it was far more active and far more selective for such operation than the undosed product.

What is claimed is:

1. In a process for making catalyst from cupreous particulates containing a major proportion of cuprous and cupric oxides and a minor proportion of elemental copper wherein a grind charge of said particulates having average particle size above 15 microns and containing up to about 10% of promoter-providing material selected from elemental aluminum and zinc, aluminum and zinc oxides, aluminum, copper and zinc chlorides, silica and aluminosilicates or 0.5% iron promoter, or below 0.05% antimony promoter is subjected to high energy comminution until the average particle size of the resulting grind is no larger than 15 microns, the improvement which comprises including in said charge about 0.05–5% of hydrated refractory metal oxide selected from hydrated alumina, hydrated oxide of titanium, hydrated oxide of zirconium and hydrated oxide of beryllium.

2. The process of claim 1 wherein said cupreous particulates contain about 75–95% cuprous oxide, about 2–10% cupric oxide, about 2–10% elemental copper, said hydrated refractory oxide is a hydrated alumina, and said grind charge has particle size no coarser than about 80 mesh.

3. The process of claim 1 wherein said cupreous particulates contain about 30–75% cuprous oxide, about 10–45% cupric oxide, about 4–25% elemental copper, said hydrated refractory oxide is a hydrated alumina, and said grind charge has at least about 95% of its particles not substantially larger than about 325 mesh.

4. The process of claim 1 wherein the major proportion of said cupreous particulates for making said grind charge are pyrometallurgically-sourced, and said refractory oxide is an alumina trihydrate.

5. Particulate high cuprous oxide catalyst for alkyl or aryl halosilane production, said catalyst consisting essentially of about 80–90% cuprous oxide, about 2–10% cupric oxide, about 2–10% elemental copper, and up to about 10% promoter selected from elemental aluminum and zinc, aluminum and zinc oxides, aluminum, copper and zinc chlorides, silica and aluminosilicates, or 0.5% iron promoter, or below 0.05% antimony promoter including about 0.05–5% of hydrated refractory metal oxide selected from hydrated alumina, hydrated oxide of titanium, hydrated oxide of zirconium and hydrated oxide of beryllium, said catalyst having surface area of about 1–8 square meters per gram, average particle size no larger than 15 microns, and exhibiting crystal lattice distortion.

6. The catalyst of claim 5 wherein said hydrated refractory oxide is a hydrated alumina.

7. The catalyst of claim 6 wherein said hydrated alumina is an alumina trihydrate.

8. Particulate medium content cuprous oxide catalyst for alkyl or aryl halosilane production, said catalyst consisting essentially of about 30–75% cuprous oxide, about 10–45% cupric oxide, about 4–25% elemental copper, and up to about 10% promoter selected from elemental aluminum and zinc, aluminum and zinc oxides, aluminum, copper and zinc chlorides, silica and aluminosilicates or 0.5% iron promoter or below 0.05% antimony promoter including about 0.05–5% of hydrated refractory metal oxide selected from hydrated alumina, hydrated oxide of titanium, hydrated oxide of zirconium and hydrated oxide of beryllium, said catalyst having specific surface area of about 1–8 square meters per gram, average particle size no larger than 15 microns, and exhibiting crystal lattice distortion.

9. The catalyst of claim 8 wherein said hydrated refractory oxide is a hydrated alumina.

10. The catalyst of claim 9 wherein said hydrated alumina is an alumina trihydrate.

* * * * *